US006849394B2

(12) United States Patent
Rozeboom et al.

(10) Patent No.: US 6,849,394 B2
(45) Date of Patent: Feb. 1, 2005

(54) COMPOSITIONS COMPRISING REPRODUCTIVE CELL MEDIA AND METHODS FOR USING SUCH COMPOSITIONS

(75) Inventors: Kevin J. Rozeboom, Mt. Horeb, WI (US); Mark E. Wilson, Madison, WI (US)

(73) Assignee: Minitube of America, Verona, WI (US)

( * ) Notice: Subject to any disclaimer, the term of this patent is extended or adjusted under 35 U.S.C. 154(b) by 0 days.

(21) Appl. No.: 10/081,097

(22) Filed: Feb. 21, 2002

(65) Prior Publication Data

US 2003/0157473 A1 Aug. 21, 2003

(51) Int. Cl.[7] .............................. A01N 1/02; A01N 1/00; C12N 5/06; C12N 5/08
(52) U.S. Cl. ............................ 435/2; 435/404; 435/405
(58) Field of Search ...................................... 435/2, 404

(56) References Cited

U.S. PATENT DOCUMENTS

| | | | | |
|---|---|---|---|---|
| 4,156,427 A | * | 5/1979 | Fahim | ......................... 604/506 |
| 5,407,913 A | * | 4/1995 | Sommer et al. | |
| 5,523,226 A | | 6/1996 | Wheeler | |
| 5,541,081 A | | 7/1996 | Hardy et al. | |
| 5,563,059 A | | 10/1996 | Alak et al. | |
| 5,693,534 A | | 12/1997 | Alak et al. | |
| 6,130,086 A | | 10/2000 | Nakazawa et al. | |
| 6,140,121 A | | 10/2000 | Ellington et al. | |
| 6,150,163 A | * | 11/2000 | McPherson et al. | ......... 435/384 |
| 6,156,569 A | | 12/2000 | Ponce de Leon et al. | |
| 6,193,647 B1 | | 2/2001 | Beebe et al. | |
| 6,194,635 B1 | | 2/2001 | Anderson et al. | |
| 6,204,240 B1 | * | 3/2001 | Gluckman et al. | |
| 6,255,109 B1 | | 7/2001 | Hansel et al. | |
| 6,271,436 B1 | | 8/2001 | Piedrahita et al. | |

OTHER PUBLICATIONS

Ovesen et al. Fertility and Sterility. 1995, vol. 63, No. 4, pp. 913–918.*
Gerfen et al. Theriogenology. 1994, 41:461–469.*
Vardinon et al. Human Reproduction. 1990, vol. 5, No. 3, pp. 294–297.*

ATCC Catalogue. ATCC Cell Lines and Hybdridomas. 1994. 8th edition. p. 518.*

Naz et al. Journal of Cellular Physiology. 1991. 146:156–163.*

Lackey et al. Archives of Andrology. 1998. 41:115–125.*

Nocera et al. American Journal of Reproductive Immunology.1995. 33:282–291.*

Quinn et al., *Fertil. Steril.* 44:493 (1985).

Boatman, In Vitro Growth of Non–Human Primate Pre– and Peri–implantation Embryos, ed. Bavister, 273–308 (New York: Plenum Press 1987).

Menezo and Khatchadourian, "The Laboratory Culture Media" *Assisted Reproductive Reviews, 1*: 136 (1991).

Leese, "Metabolism of the Preimplantation Mammalian Embryo" Oxford Reviews of Reproductive Biology, 13:35–72 (1991) ed. S.R. Milligan, Oxford University Press.

Waberski, et al., "Fertility of long–term–stored boar semen : Influence of extender (Androhep and Kiev) , storage time and plasma droplets in the semen" Animal Repro Sci 36:145–151 (1994).

* cited by examiner

*Primary Examiner*—Vera Afremova
(74) *Attorney, Agent, or Firm*—Michael Best & Friedrich LLP; Jeffrey S. Ward; Wendy M. Seffrood

(57) ABSTRACT

Disclosed are compositions for mammalian, avian or piscian reproductive cells and methods for the collection, holding, processing, in vitro fertilization, sexing culturing, or storing (including long-term cryopreservation) of mammalian, avian, or piscian reproductive sperm cells. The compositions comprise a suitable reproductive cell media and a transforming growth factor, an insulin-like growth factor, or zinc, and, optionally, inositol, transferrin, or fructose, or combinations thereof.

27 Claims, No Drawings

COMPOSITIONS COMPRISING REPRODUCTIVE CELL MEDIA AND METHODS FOR USING SUCH COMPOSITIONS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Artificial insemination (AI), along with in vitro fertilization and embryo transplantation, afford enhanced reproduction in mammals, including livestock, and offer many advantages over direct mating. In the livestock breeding art, these techniques permit wider dissemination of desirable genetic features. Semen collected from a single male can be used to inseminate multiple females, thereby reducing the number of males required to maintain a population. Artificial insemination techniques permit greater control over breeding, which results in greater reproducibility and facilitates maintenance of large-scale operations.

Maintaining the viability of reproductive cells is an important aspect of artificial insemination and other techniques used in indirect breeding. The processing requirements for semen used in AI may vary according to the species of animal. Bovine insemination requires relatively low concentrations of semen, and a suitable sample may be rapidly frozen in a narrow diameter straw and stored for an extended period of time without adversely affecting the fertility of the sample. In contrast, porcine semen is not susceptible to this approach, because greater numbers of sperm cells and larger volumes of semen or diluted semen are required to inseminate sows. Insemination using frozen boar semen has not been sufficiently satisfactory to justify widespread use of this technique. Boar semen is generally diluted or extended with a suitable storage medium and cooled to a temperature of about 17° C. prior to transport. The culture medium serves to increase the total volume of the sample and provide nutrients to maintain the sperm cells. Significant loss of sperm cell vitality occurs after storing the semen for just a few days. Currently, the best medium generally maintains boar sperm cell viability for about five to seven days. The relatively short time that boar semen can be stored imposes considerable constraints on the distribution of boar semen for AI. Other animals, such as horses, produce sperm cells that also suffer from short-lived viability.

Artificial insemination, in vitro fertilization, and embryo transfer technology are also used in humans to aid in the conception process, and/or as a solution to various physiological problems relating to infertility. Clearly, maintaining the viability of reproductive cells for these uses is also very important.

BRIEF SUMMARY OF THE INVENTION

In one aspect, the present invention provides a composition comprising a reproductive cell medium for mammalian, avian, or piscian reproductive cells, wherein the medium comprises at least one growth factor selected from the group consisting of insulin-like growth factor (IGF) and transforming growth factor (TGF).

In another aspect, the present invention provides a composition comprising a reproductive cell medium for mammalian, avian, or piscian reproductive cells, wherein the medium comprises zinc.

Other aspects of the invention include compositions comprising reproductive cell media for mammalian, avian, or piscian reproductive cells, wherein the media comprise one or both of (1) at least one growth factor selected from the group consisting of insulin-like growth factor (IGF) and transforming growth factor (TGF); and (2) zinc, in combination with at least one component selected from the group consisting of inositol, fructose, transferrin, and combinations thereof.

In yet another aspect, the present invention provides a method for storing mammalian, avian, or piscian reproductive cells comprising contacting the cells with the above compositions.

BRIEF DESCRIPTION OF THE DRAWINGS

Not applicable.

DETAILED DESCRIPTION OF THE INVENTION

The present invention provides compositions comprising reproductive cell media for mammalian, avian, or piscian reproductive cells, and particularly provides compositions comprising sperm cell media for mammalian, avian, or piscian sperm cells. As used herein, the term "reproductive cells" encompasses sperm cells, oocytes, and embryos of any mammal, bird, or fish, including livestock (e.g., pigs, cows, horses, sheep and the like) and humans. Further, the terms "medium for mammalian, avian, or piscian reproductive cells", "reproductive cell media for mammalian, avian, or piscian reproductive cells", or "reproductive cell medium" refer to any medium used for the collection, holding, processing, in vitro fertilization, sexing, culturing, or storing (including long-term cryopreservation) of mammalian, avian, or piscian reproductive cells, and includes both solid and liquid compositions, as well as solid compositions that are reconstituted or mixed with a liquid carrier, such as water, for use. The term "sperm cell medium" refers to any medium used for the collection, holding, processing, in vitro fertilization, sexing, culturing, or storing (including long-term cryopreservation) of mammalian, avian or piscian sperm cells and/or semen.

Many specific media formulations are known or are available commercially, including short-term, medium-term, and long-term extenders for preserving semen. Typically, storage media formulations are provided in solid form, and are diluted with water for use. Standard formulations (e.g., Androhep Plus™ and BTS) can be found in the art. For example, see Waberski et al. *Animal Reproduction Sci.* 36:145–151 (1994), which is incorporated herein in its entirety.

The reproductive cell medium herein is generally one containing physiologically balanced salts, energy sources, and antibiotics and is suitable for the species whose reproductive cells are being treated. Typically, suitable media contain at least one buffer (e.g., sodium bicarbonate or HEPES) and a carbon source (e.g., glucose). Additional components may include ethylene diamine tetraacetic acid (EDTA), bovine serum albumin (BSA), and one or more antibiotics. Examples of suitable media for certain species such as humans and monkeys include: human tubal fluid (HTF), as obtained from Quinn et al., Fertil. Steril., 44: 493 (1985), supplemented with 10% heat-inactivated maternal or fetal cord serum, which is typically used for IVF and embryo culture; TALP, as obtained from Boatman, in In Vitro Growth of Non-Human Primate Pre- and Peri-implantation Embryos, ed. Bavister, pp. 273–308 (New York: Plenum Press, 1987); Ham's F-10 medium, Menezo's B.sub.2 medium (BioMerieux SA, France), Earles medium (Sigma Chemical Co., St. Louis, Mo.), and the like. General reviews describing these types of media include Menezo and Khatchadourian, "The Laboratory Culture Media," Assisted Reproduction Reviews, 1: 136 (1991) and Lease, "Metabolism of the Preimplantation Mammalian Embryo," Oxford Reviews of Reproductive Biology, 13: 35–72 (1991), ed. S. R. Milligan, Oxford University Press. The practitioner will be able to devise the necessary medium suitable for the species and the reproductive cell type. The pH of the medium is generally about 7 to 8, more preferably about 7.2–7.6.

In a first aspect, the present invention provides a composition comprising a reproductive cell medium for mammalian, avian, or piscian reproductive cells, particularly a sperm cell medium for mammalian, avian or piscian sperm cells, where the medium comprises at least one growth factor selected from the group consisting of transforming growth factor ("TGF") and insulin-like growth factor ("IGF"). Here, TGF refers to any type of transforming growth factor, including but not limited to TGFβ, such as TGFβ-1 and TGFβ-2. Likewise, IGF refers to any type of insulin-like growth factor, including but not limited to IGF-1. The sperm cell media of the present invention are particularly useful with porcine sperm cells.

Preferably, both TGF and IGF are present in the media of the present invention. More preferably still, a given medium comprises TGFβ-1, TGFβ-2, and IGF-1. These growth factors may be obtained from any commercially available source.

It is also preferred that the growth factor be present in a given medium in its "activated" form. By "activated growth factor," it is meant growth factor that contains some unbound growth factor. Unbound growth factor is defined as growth factor that is not bound by a carrier protein. Growth factor that is bound by albumin is also defined as unbound growth factor. As one of skill in the art will appreciate, a preparation of growth factor that is activated and which thus comprises some unbound growth factor may also comprise some latent (bound) growth factor. Preferably, a preparation of activated growth factor comprises one or more of activated TGFβ-1, TGFβ-2, and IGF-1. More preferably, a preparation of activated growth factor comprises at least 75% unbound TGFβ-1, TGFβ-2 and/or IGF-1. Still more preferably, activated growth factor comprises at least 90% unbound TGFβ-1, TGFβ-2 and/or IGF-1.

One wishing to determine the percentage of activation for a given growth factor present in a preparation of growth factor may do so using any suitable means. Conveniently, the amount of a given activated growth factor may be quanitfied using an immunoassay employing an antibody specific for that activated growth factor. The total amount of that growth factor (i.e., activated and latent growth factor) may be quantitated by first lowering the pH of the growth factor preparation to about 2.5, which releases the growth factor from the carrier protein, and then performing the immunoassay. The latent growth factor in a preparation may be calculated indirectly by subtracting the activated growth factor from the total growth factor. An immunoassay system for assaying activated IGF-1 is available from BioSource Europe S.A. (Nivelles Belgium); immunoassay systems for assaying TGFβ-1 and TGFβ-2 are available from Promega Corporation (Madison, Wis.).

The TGF and/or IGF may be present in a given medium of the invention in any amount desired by the medium formulator. The amounts below are expressed as the concentration of a given growth factor in a composition when the medium is in the liquid state upon reconstitution, dilution, or mixing with water or other suitable carriers, and again, each specific growth factor may be used alone, or in combination with other growth factors. Suitably, TGF may be present as TGFβ-1 in a concentration of from about 0.1 ng/L to about 10 μg/L and/or as TGFβ-2 in a concentration of from about 0.1 ng/L to about 200 ng/L; IGF may be present as IGF-1 in a concentration of from about 0.1 ng/L to about 50 μg/L.

Preferably, TGF may be present as TGFβ-1 in a concentration of from about 20 ng/L to about 400 ng/L and/or as TGFβ-2 in a concentration of from about 0.4 ng/L to about 16 ng/L; IGF may be present as IGF-1 in a concentration of from about 40 ng/L to about 640 ng/L. Most preferably, TGF is present in a given medium as TGFβ-1 in a concentration of from about 50 ng/L to about 150 ng/L and/or as TGFβ-2 in a concentration of from about 1.8 ng/L to about 3.8 ng/L; IGF is most preferably present as IGF-1 in a concentration of from about 200 ng/L to about 450 ng/L. Of course, the concentration of growth factor present in a given medium can depend on several factors, including the degree to which the growth factor is activated, and the type of mammalian, avian or piscian reproductive cells with which the medium is to be used.

The optimal concentration of growth factor to be used for a given medium in the compositions of the present invention can also be determined by preparing a series of media with differing concentrations of growth factor and comparing the efficacy of those media for use with a given type of mammalian, avian or piscian reproductive cell or cells. For example, where porcine semen is used, efficacy can be determined using one or more known measurements of sperm cell viability, including both in vitro and in vivo techniques. For example, motility is one indicia of sperm cell viability. Increased motility of sperm cells stored in supplemented storage medium relative to the motility of sperm cells stored in unsupplemented storage medium is indicative of enhanced viability. Enhanced viability of stored sperm is also suggested by reduced percentages of uncapacitated sperm, increased competitive binding to oocytes, or increased pregnancy rates or litter size following artificial insemination using stored semen. Similarly, enhanced viability of sperm, oocytes, or embryos can be indicated by increased pregnancy rates or litter size following in vitro fertilization and embryo transfer.

In a second aspect, the invention provides a composition comprising a reproductive cell medium for mammalian, avian, or piscian reproductive cells, wherein the medium comprises zinc. Zinc may be added as zinc sulfate, zinc proteinate, or zinc chloride, and to give a final concentration of zinc in the medium of from about 0.1 mg/L to about 300 mg/L. Preferably, the final concentration of zinc is from about 28 mg/L to about 60 mg/L. Again, optimal concentrations for a given medium can be determined as described above with respect to growth factor concentrations.

The media of the invention may also comprise both growth factor and zinc, in the concentrations set forth above for each component.

The media of the invention may also comprise one or more of inositol, transferrin, and fructose, in addition to the growth factor and/or zinc. If used, the inositol should be present in a concentration of from about 0.1 mg/L to about 1 g/L. Again, the concentration of inositol in a given medium may be adjusted depending upon the specific mammalian reproductive cells to be stored.

The use of transferrin, as opposed to apo-transferrin or holo-transferrin, is preferred. Transferrin may be present in a concentration of from about 0.5 mg/L to about 10 mg/L, with a concentration of from about 2.5 mg/L to about 5 mg/L being preferred.

If fructose is used, it may be present in a concentration of from about 0.1 g/L to about 24 g/L. A concentration of from about 4 g/L to about 8 g/L is preferred.

One of ordinary skill in the art may prepare a composition of the present invention using any suitable means. For example, to obtain a certain volume of medium, the appropriate mass of the individual components needed to obtain the desired final concentration may be combined with water or other suitable solvent and brought to the desired final volume. The media may be conveniently prepared as a solid, blended formulation in which each of the individual components, including TGF, IGF, or zinc, is added in dry form and the components blended together for later reconstitution to give the desired final concentration of each component. A suitable commercially available dry medium and the desired amount of TGF, IGF, or zinc, for example, could be reconstituted in water to obtain a medium with the desired final concentration of components. It is envisioned that concentrated stock solutions of the media of the invention may be prepared and subsequently diluted to achieve the appropriate final concentration of components in the medium prior to use.

The concentrations of components expressed herein are given as the final concentration of components in the medium for reproductive cells. One skilled in the art would appreciate that the dry blended formula is formulated such that the masses of each individual media component in the dry blended formula are present in an amount sufficient to give the desired concentration of each of the individual components when the blended formula is reconstituted with a suitable volume of water. The concentration of each component of interest (e.g., growth factor, zinc, inositol, transferrin, or fructose) may also be expressed in terms of the units of mass of each component of interest per unit of mass of the dry blended media. It will be appreciated by one skilled in the art that concentrations expressed on a weight by weight basis may vary depending on the mass contribution of other components in the medium.

Concentrations of components in liquid medium are expressed in terms of the number of units mass per liter. One of skill in the art would appreciate that the medium of the present invention may be prepared in any volume, and the invention is not intended to be limited to media prepared in one liter volumes.

In another aspect, the present invention provides a method of storing mammalian, avian, or piscian reproductive cells comprising contacting the cells with the compositions of the present invention. Typically, as stated above, the compositions of the invention will be provided in solid form. It should then be diluted with Type I water, approximately one hour prior to use. Preferably, a sample comprising the cells is collected by any suitable means and placed in contact with a given amount of composition in liquid form as soon as possible following collection. The contacting step should be performed in such a manner that mechanical or other injury to the cells is minimized. Following the contacting step, the mixture of cells and composition are preferably equilibrated to and held at a suitable temperature for maintaining the viability, of the cells until use. The temperature at which the cells are suitably maintained will depend on the type of cell, medium, and application.

The following non-limiting examples are intended to be purely illustrative.

EXAMPLES

In the examples below, commercially available semen extenders, including Androhep Plus™ (Minitube of America, Verona, Wis.), were combined with TGF, IGF, or zinc, and water, or optionally further combined with inositol, transferrin, and fructose to prepare compositions comprising sperm cell media according to the present invention. The compositions were evaluated for their ability to enhance or extend the viability of stored boar semen.

Treatment Preparation

Compositions comprising sperm cell media were prepared prior to collection by reconstituting Androhep Plus™ and the individual components indicated in the experiments below with microfiltered, deionized (Type I) water. Androhep Plus™ was prepared according to the manufacturer's instructions, except that additional components were added in an amount sufficient to give the concentrations indicated below. Each composition was transferred in 75-ml aliquots to 100-ml plastic bottles commercially available from Minitube of America (Verona, Wis.).

Semen Collection, Processing, and Storage

Semen was collected (modified full ejaculate) from randomly selected, sexually mature boars (n=3) using the gloved hand technique. Following each collection, each ejaculate was evaluated for sperm cell concentration with an SDM5 photometer with a 546 nm filter and the percentage of motile cells was assessed with Sperm Vison™ using a plain glass slide and a 6 µl drop of semen. Aliquots of semen containing $1 \times 10^9$ motile spermatozoa from each of the three boars was transferred into each 75-ml aliquot of composition comprising sperm cell medium at the same temperature (36° C.±1° C.) to give a final concentration of $4 \times 10^7$ live sperm cells/ml. Following dispersion of the sperm cells in the composition, each sample was tested for percent motility.

Maintenance of Samples and Data Collection

Samples were maintained in a semen storage unit at 17° C. The samples were gently mixed periodically during storage. At days 5, 10, and 20, the sample was mixed and a five-ml aliquot was removed for testing. Each aliquot was pre-warmed for 30 minutes in a dry block heater at 37° C. prior to motility testing. Motility testing was which was performed using the Sperm Vison™ module in the Prism Program and a plain glass slide pre-warmed to 37° C.

Effect of Growth Factor in the Absence of Antibiotic on Sperm Motility

The ability of growth factor to enhance sperm viability of stored semen was assessed by evaluating the motility of sperm in semen stored in a composition comprising a sperm cell medium, where the medium comprised growth factor, and comparing that sperm motility to the motility of sperm in semen samples stored in compositions comprising a sperm cell medium, where the medium did not contain any growth factor.

Example 1

Sperm cell media were prepared by combining Androhep Plus™, without the antibiotic normally present in Androhep Plus™ and growth factor to give final concentrations of 0–160 ng/L TGFβ-1, 0–6.4 ng/L TGFβ-2, and 0–640 ng/L IGF-1. Sperm motility was assessed at days 1, 5, 10, and 20.

The data are summarized in Table 1 in terms of mean percent motility, based on assessment of twenty-seven samples for each medium tested.

TABLE 1

Effect of growth factor concentration on motility of sperm in semen stored in medium (Androhep Plus ™) containing no antibiotic.

| Concentration of growth factor (ng/L) | | Day | Mean % motility |
|---|---|---|---|
| TGFβ-1 | 0 | 1 | 76.0 |
| TGFβ-2 | 0 | 5 | 88.1 |
| IGF | 0 | 10 | 54.0 |
| | | 20 | 7.3 |
| TGFβ-1 | 20 | 1 | 84.3 |
| TGFβ-2 | 0.8 | 5 | 92.3 |
| IGF | 80 | 10 | 68.3 |
| | | 20 | 3.0 |
| TGFβ-1 | 40 | 1 | 71.0 |
| TGFβ-2 | 1.6 | 5 | 93.7 |
| IGF | 160 | 10 | 68.3 |
| | | 20 | 6.7 |
| TGFβ-1 | 80 | 1 | 82.3 |
| TGFβ-2 | 3.2 | 5 | 92.4 |
| IGF | 320 | 10 | 60.0 |
| | | 20 | 6.3 |
| TGFβ-1 | 160 | 1 | 89.0 |
| TGFβ-2 | 6.4 | 5 | 90.4 |
| IGF | 640 | 10 | 87.3 |
| | | 20 | 15.3 |

Example 2

In another study, sperm cell media were prepared containing Androhep Plus™ and varying concentrations of growth factor (0–160 ng/L TGFβ-1, 0–6.4 ng/L TGFβ-2, and 0–640 ng/L IGF-1). Freshly collected semen samples were transferred to aliquots of media and sperm motility was assessed at days 1, 5, 10, and 20. The data are summarized in Table 2 below in terms of mean percent motility, based on assessment of twenty-seven samples for each medium tested.

TABLE 2

Effect of growth factor concentration on motility of sperm in semen stored in Androhep Plus ™

| Concentration of growth factor (ng/L) | | Day | Mean % motility |
|---|---|---|---|
| TGFβ-1 | 0 | 1 | 94.3 |
| TGFβ-2 | 0 | 5 | 92.7 |
| IGF | 0 | 10 | 83.3 |
| | | 20 | 0.0 |
| TGFβ-1 | 20 | 1 | 81.3 |
| TGFβ-2 | 0.8 | 5 | 90.7 |
| IGF | 80 | 10 | 90.0 |
| | | 20 | 18.7 |
| TGFβ-1 | 40 | 1 | 85.3 |
| TGFβ-2 | 1.6 | 5 | 93.0 |
| IGF | 160 | 10 | 86.7 |
| | | 20 | 38.0 |
| TGFβ-1 | 80 | 1 | 85.7 |
| TGFβ-2 | 3.2 | 5 | 94.0 |
| IGF | 320 | 10 | 87.3 |
| | | 20 | 39.7 |
| TGFβ-1 | 160 | 1 | 59.7 |
| TGFβ-2 | 6.4 | 5 | 94.3 |
| IGF | 640 | 10 | 85.3 |
| | | 20 | 43.0 |

Example 3

Sperm cell media were prepared using base Androhep Plus™, lacking the antibiotic normally present in Androhep Plus™, and varying concentrations of growth factors (0–400 ng/L TGFβ-1, 0–16 ng/L TGFβ-2, and 0–1600 ng/L IGF-1). Freshly collected semen samples were transferred to aliquots of media and sperm motility was assessed at days 1, 5, 10, and 20. The data are summarized in Table 3 below, in terms of mean percent motility, based on assessment of twenty-seven samples for each medium tested.

TABLE 3

Effect of growth factor concentration on motility of sperm in stored semen (Androhep Plus ™ + growth factors and no antibiotic)

| Concentration of growth factor (ng/L) | | Day | Mean % motility |
|---|---|---|---|
| TGFβ-1 | 0 | 1 | 94.7 |
| TGFβ-2 | 0 | 5 | 90.3 |
| IGF | 0 | 10 | 89.9 |
| | | 20 | 20.0 |
| TGFβ-1 | 20 | 1 | 93.7 |
| TGFβ-2 | 0.8 | 5 | 87.3 |
| IGF | 80 | 10 | 75.0 |
| | | 20 | 6.0 |
| TGFβ-1 | 40 | 1 | 97.3 |
| TGFβ-2 | 1.6 | 5 | 89.3 |
| IGF | 160 | 10 | 90.7 |
| | | 20 | 0.0 |
| TGFβ-1 | 400 | 1 | 96.3 |
| TGFβ-2 | 16 | 5 | 87.3 |
| IGF | 1600 | 10 | 92.7 |
| | | 20 | 5.0 |

Example 4

The effect of growth factor concentration on the motility of sperm in stored semen was evaluated using various formulations of sperm cell media prepared using various concentrations of growth factor (0–40 ng/L TGFβ-1, 0–1.6 ng/L TGFβ-2, and 0–160 ng/L IGF-1), and Androhep Plus™. Freshly collected semen samples were transferred to aliquots of media and sperm motility was assessed at days 1, 5, 10, and 20. The data are summarized in Tables 4 and 5. Table 4 shows the mean percent motility averaged for days 1, 5, 10, and 20 at different concentrations of growth factor, based on assessment of twenty-seven samples for each medium tested.

Table 5 shows the mean percent motility for at different concentrations of growth factor as a function of time, based on assessment of twenty-seven samples for each medium tested.

TABLE 4

Comparison of effect of growth factor concentration on motility of sperm in stored semen in Androhep Plus ™.

| Concentration of growth factor (ng/L) | | Mean % motility |
|---|---|---|
| TGFβ-1 | 0 | 72.3 |
| TGFβ-2 | 0 | |
| IGF | 0 | |
| TGFβ-1 | 10 | 76.9 |
| TGFβ-2 | 0.4 | |
| IGF | 40 | |
| TGFβ-1 | 20 | 74.8 |
| TGFβ-2 | 0.8 | |
| IGF | 80 | |
| TGFβ-1 | 40 | 76.5 |
| TGFβ-2 | 1.6 | |
| IGF | 160 | |

TABLE 5

Comparison of effect of growth factor concentration on motility of sperm in stored semen in Androhep Plus ™ as a function of time

| Concentration of growth factor (ng/L) | | Day | Mean % motility |
|---|---|---|---|
| TGFβ-1 | 0 | 1 | 87.6 |
| TGFβ-2 | 0 | 5 | 85.7 |
| IGF | 0 | 10 | 74.4 |
| | | 20 | 14.6 |
| TGFβ-1 | 10 | 1 | 88.6 |
| TGFβ-2 | 0.4 | 5 | 86.4 |
| IGF | 40 | 10 | 79.9 |
| | | 20 | 21.6 |
| TGFβ-1 | 20 | 1 | 88.5 |
| TGFβ-2 | 0.8 | 5 | 83.8 |
| IGF | 80 | 10 | 83.6 |
| | | 20 | 15.3 |
| TGFβ-1 | 40 | 1 | 88.9 |
| TGFβ-2 | 1.6 | 5 | 85.2 |
| IGF | 160 | 10 | 77.7 |
| | | 20 | 32.0 |

Example 5

The effect of zinc concentration on motility of sperm in stored semen was evaluated using sperm cell media prepared using base Androhep Plus™, and from 0.05 g/L to 1 g/L ZnCl. Freshly collected semen samples were transferred to aliquots of media and sperm motility was assessed at days 1, 5, 10, and 20. The data are summarized in Table 6 below, in terms of mean percent motility, based on assessment of twenty-seven samples for each medium tested.

TABLE 6

Comparison of effect of zinc concentration on motility of sperm in stored semen as a function of time

| Concentration of zinc sulfate (g/L) | Day | Mean % motility |
|---|---|---|
| 0 | 1 | 88.3 |
| | 5 | 89.7 |
| | 10 | 84.0 |
| | 20 | 77.0 |
| 0.05 | 1 | 83.3 |
| | 5 | 83.7 |
| | 10 | 87.7 |
| | 20 | 84.0 |
| 0.1 | 1 | 92.0 |
| | 5 | 93.3 |
| | 10 | 89.7 |
| | 20 | 78.3 |
| 0.2 | 1 | 94.7 |
| | 5 | 93.3 |
| | 10 | 87.7 |
| | 20 | 87.0 |
| 0.5 | 1 | 86.0 |
| | 5 | 85.7 |
| | 10 | 89.3 |
| | 20 | 82.5 |
| 1.0 | 1 | 94.0 |
| | 5 | 73.0 |
| | 10 | 87.3 |
| | 20 | 78.3 |

Example 6

The effect of fructose concentration on the motility of sperm in stored semen was evaluated in sperm cell media prepared using Androhep Plus™, growth factor (20 ng/L TGFβ-1, 0.8 ng/L TGFβ-2, and 80 ng/L IGF-1), and from 0 g/L to 30 g/L fructose. Freshly collected semen samples were transferred to aliquots of media and sperm motility was assessed at days 1, 5, 10, and 20. The data are summarized in Table 7 below, in terms of mean percent motility, based on assessment of twenty-seven samples for each medium tested.

TABLE 7

Comparison of effect of fructose concentration on motility of sperm in stored semen as a function of time.

| Concentration of fructose (g/L) | Day | Mean % motility |
|---|---|---|
| 0 | 1 | 92.4 |
| | 5 | 86.7 |
| | 10 | 86.3 |
| | 20 | 86.8 |
| 3.75 | 1 | 94.9 |
| | 5 | 88.7 |
| | 10 | 88.7 |
| | 20 | 89.8 |
| 7.5 | 1 | 96.9 |
| | 5 | 91.0 |
| | 10 | 88.3 |
| | 20 | 89.8 |
| 15 | 1 | 94.3 |
| | 5 | 85.8 |
| | 10 | 89.3 |
| | 20 | 89.3 |
| 30 | 1 | 94.7 |
| | 5 | 54.8 |
| | 10 | 37.4 |
| | 20 | 2.2 |

Example 7

The effect of inositol concentration on the motility of sperm in stored semen was evaluated in sperm cell media prepared using Androhep Plus™, and varying concentrations of inositol (0–500 mg inositol/L). Freshly collected semen samples were transferred to aliquots of media and sperm motility was assessed at days 1, 5, 7, 10, and 20. The data are shown in Table 8 below, in terms of mean percent motility, based on assessment of twenty-seven samples for each medium tested.

TABLE 8

Comparison of effect of inositol concentration on motility of sperm in stored semen as a function of time

| Concentration of inositol (g/L) | Day | Mean % motility |
|---|---|---|
| 0 | 1 | 78.7 |
| | 5 | 92.7 |
| | 7 | 93.0 |
| | 10 | 84.3 |
| | 20 | 68.3 |
| 0.25 | 1 | 85.7 |
| | 5 | 88.0 |
| | 7 | 93.3 |
| | 10 | 78.3 |
| | 20 | 48.0 |
| 0.5 | 1 | 94.7 |
| | 5 | 93.3 |
| | 7 | 92.7 |
| | 10 | 84.3 |
| | 20 | 70.3 |

The present invention is not limited to the exemplified embodiments, but is intended to encompass all such modifications and variations as come within the scope of the following claims.

What is claimed is:

1. A composition comprising a sperm cell and a medium, wherein the medium comprises at least one insulin-like growth factor and at least one transforming growth factor, and wherein the medium is a collection, holding, processing, in vitro fertilization, sexing, culturing or storage medium.

2. The composition of claim 1, wherein the sperm cell is a mammalian sperm cell.

3. The composition of claim 2, wherein the sperm cell is a porcine sperm cell.

4. The composition of claim 2, wherein the sperm cell is an equine sperm cell.

5. The composition of claim 2, wherein the sperm cell is a bovine sperm cell.

6. The composition of claim 2, wherein the sperm cell is an ovine sperm cell.

7. The composition of claim 2, wherein the sperm cell is a human sperm cell.

8. The composition of claim 1, wherein the sperm cell is an avian sperm cell.

9. The composition of claim 1, wherein the sperm cell is a piscian sperm cell.

10. The composition of claim 1, wherein the transforming growth factor comprises TGF$\beta$-1.

11. The composition of claim 1, wherein the transforming growth factor comprises TGF$\beta$-2.

12. The composition of claim 1, wherein the transforming growth factor comprises TGF$\beta$-1 and TGF$\beta$-2.

13. The composition of claim 1, wherein the insulin-like growth factor comprises IGF$\beta$-1.

14. The composition of claim 12, wherein the medium further comprises IGF$\beta$-1.

15. The composition of claim 1, wherein the medium further comprises at least one component selected from the group consisting of inositol, transferrin, and fructose.

16. The composition of claim 10, wherein the medium is in liquid form and the TGF$\beta$-1 is present in a concentration from about 0.1 ng/L to about 10 $\mu$L.

17. The composition of claim 16, wherein the TGF$\beta$-1 is present in a concentration from about 20 ng/L to about 400 ng/L.

18. The composition of claim 17, wherein the TGF$\beta$-1 is present in a concentration from about 50 ng/L to about 150 ng/L.

19. The composition of claim 11, wherein the medium is in liquid form and the TGF$\beta$-2 is present in a concentration from about 0.1 ng/L to about 200 ng/L.

20. The composition of claim 19, wherein the TGF$\beta$-2 is present in a concentration from about 0.4 ng/L to about 16 ng/L.

21. The composition of claim 19 wherein the TGF$\beta$-2 is present in a concentration from about 1.8 ng/L to about 3.8 ng/L.

22. The composition of claim 13, wherein the medium is in liquid form and the IGF-1 is present in a concentration from about 0.1 ng/L to about 30 $\mu$g/L.

23. The composition of claim 22 wherein the IGF-1 is present in a concentration from about 40 ng/L to about 640 ng/L.

24. The composition of claim 22, wherein the IGF-1 is present in a concentration from about 200 ng/L to about 450 ng/L.

25. The composition of claim 1, wherein the medium further comprises a cryopreservative.

26. The composition of claim 1, wherein the medium further comprises zinc.

27. The composition of claim 3, wherein the medium comprises TGF$\beta$-1, TGF$\beta$-2, and IGF-1.

* * * * *